United States Patent

Quentin et al.

[11] Patent Number: 6,121,239
[45] Date of Patent: Sep. 19, 2000

[54] PEPTIDE SUBSTRATES FOR THE IDENTIFICATION OF FACTOR XA

[75] Inventors: Gérard Quentin, Colombes; Jean-Luc Martinoli, Villeneuve-la-Garenne, both of France

[73] Assignee: Serbio, Gennevilliers, France

[21] Appl. No.: 07/768,710

[22] PCT Filed: Dec. 31, 1990

[86] PCT No.: PCT/FR90/00974

§ 371 Date: Oct. 18, 1991

§ 102(e) Date: Oct. 18, 1991

[87] PCT Pub. No.: WO91/12338

PCT Pub. Date: Aug. 22, 1991

[30] Foreign Application Priority Data

Feb. 19, 1990 [FR] France ................... 90 01965

[51] Int. Cl.[7] ............ A61K 38/00; A61K 38/06; A61K 38/36
[52] U.S. Cl. ............... 514/18; 530/331; 435/13
[58] Field of Search .............. 530/330, 331; 435/13; 514/18

[56] References Cited

U.S. PATENT DOCUMENTS 4,508,644  4/1985  Heber et al. .................. 530/331

FOREIGN PATENT DOCUMENTS 0025190  3/1981  European Pat. Off. .
0280610  8/1988  European Pat. Off. .

OTHER PUBLICATIONS

Morrison & Boyd, *Organic Chemistry* (3rd Ed.). Allyn & Bacon Inc. (1973) 1147–1149.

*Primary Examiner*—Michael P. Woodward
*Assistant Examiner*—Michael Borin
*Attorney, Agent, or Firm*—Ostrolenk, Faber, Gerb & Soffen, LLP

[57] ABSTRACT

Peptide substrates selected from the group consisting of (i) the tri- and tetra-peptides of the formula $$Q-A_1-A_2-Gly-A_4-R \qquad (I)$$

having SEQ ID NO: 1 in which Q is a group which blocks the N-termnal end of the peptide chain, $A_1$ is selected from the group consisting of Leu, Ile, Nle, Nva, CHA, CHG, CHT, Phe, Ala and Lys groups, where the basic side-group of the Lys residue is blocked with a suitable group which substantially removes the basic character of said side-group, $A_2$ is a single bond, Asp or Glu, the carboxylic acid side-group of Asp and Glu being capable of esterification or amidation, $A_4$ is selected from the group consisting of Arg and Lys groups, and R is pNA; and (ii) their addition salts. These peptide substrates are useful in the determination of Factor Xa.

3 Claims, No Drawings

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: Region
        (B) LOCATION: 1
        (D) OTHER INFORMATION: /label= amino_acid-1
            /note= "Leu, Ile, Nle(Norleucine), Nva(Norvaline),
            Phe, Ala, Lys, CHA(3-cyclohexylalanyl),
            CHG(alpha-cyclohexylglycl) or
            CHT(3-(4-hydroxycyclohexyl)alanyl)"

(ix) FEATURE:
        (A) NAME/KEY: Region
        (B) LOCATION: 2
        (D) OTHER INFORMATION: /label= amino_acid-2
            /note= "Asp or Glu"

(ix) FEATURE:
        (A) NAME/KEY: Region
        (B) LOCATION: 4
        (D) OTHER INFORMATION: /label= amino_acid-4
            /note= "Arg or Lys"

(xi) SEQUENCE DESCRIPTION: SEQ ID NO:1:

Xaa Xaa Gly Xaa

PEPTIDE SUBSTRATES FOR THE IDENTIFICATION OF FACTOR XA

FIELD OF THE INVENTION

The present invention relates, by way of novel industrial products, to tri- and tetra-peptide compounds. These novel products are particularly useful as substrates for the identification and assay of Factor Xa (i.e. activated Factor X) involved in the mechanisms of hemostasis. The invention further relates to the method of preparing these novel products and to the method of assaying and/or identifying Factor Xa by means of said products.

PRIOR ART

The enzymes belonging to the class E.C. 3.4.21 [as defined in the work "Enzyme Nomenclature", Elsevier Scientific Publishing Company, Amsterdam 1973, pages 238 et seq. (former nomenclature: class E.C. 3.4.4)] are known to be substances which cleave the amide linkages of the protein or peptide backbone at the carboxyl group of Arg, Lys, Orn and His residues. This cleavage mechanism is well known to those skilled in the art and is amply exemplified in the documents of the prior art cited below.

The currently used substrates for enzymes belonging to said class are essentially tri- or tetra-peptide compounds whose N-terminal end is generally substituted by a blocking group such as benzoyl, benzyloxycarbonyl, t-butoxycarbonyl, t-amyloxycarbonyl, tosyl, acetyl or the like and whose CO-terminal end is amidated by an aminated group which can be a radioactive radical or a radical, especially a p-nitroanilino group, capable of imparting coloration or fluorescence before or (preferably) after cleavage. Reference is made in this connection to the following patent documents: FR-A-2 372 798, EP-A-0 004 256, U.S. Pat. Nos. 4,508,644, 4,448,715, FR-A-2 471 411, FR-A-2 317 280 and FR-A-2 459 226.

It is found that the peptide derivatives in the patent documents cited above have little affinity for water. They have a low solubility or dispersibility in water; consequently, it is sometimes necessary to add an organic solvent to make them usable. The systems comprising mixed solvents are scarcely compatible, in general terms, with biological media: they cause either a decrease in the activity of the substrate or, in certain cases, a deterioration in the enzyme which it is desired to assay. Furthermore, the low affinity of these substrates for water causes a decrease in the sensitivity of the enzyme assay methods.

To improve the solubility of enzyme substrates in water, EP-A-0 025 190 has disclosed a first technical solution which consists in substituting, on said N-terminal end, a polyethylene glycol residue monoetherified by an alkyl group, for example Me—O(CH$_2$CH$_2$O)$_x$—CO (in which X is an integer such that the polyethylene glycol residue has an average molecular weight of about 600), the amino acid residue containing the CO-terminal end of the peptide chain being other than the Arg and Lys residues which are present according to the invention, as will be seen below; also, EP-A-0 280 610 (to the Applicant) has disclosed another technical solution which consists in attaching an alkoxycarbonylmethylenecarbonyl radical, such as the methoxymalonyl radical (i.e. Me—O—CO—CH$_2$—CO, abbreviated to MM), to the N-terminal end of a dipeptide.

Furthermore, according to document EP-A-0 280 610 cited above, dipeptide substrates containing said methoxymalonyl radical on said N-terminal end are generally presented as being more sensitive towards enzymes belonging to the class E.C. 3.4.21 than tri- and tetra-peptide substrates containing said methoxymalonyl radical. However, according to EP-A-0 280 610, these dipeptide substrates are not particularly specific towards Factor Xa and do not permit an effective assay of said Factor Xa.

Factor Xa, which belongs to the subclass E.C. 3.4.21.6, is known to be one of the important components involved in the mechanisms of hemostasis. The activation of Factor X leads to the formation of Factor Xa, which is a serine protease responsible for the conversion of prothrombin to thrombin. It is therefore of very great interest, from the diagnostic point of view, to have peptide substrates which are specific for Factor Xa and which can be used by a simple determination technique before any adverse thromboembolic accident.

It is known that tri- and tetra-peptide substrates have already been recommended for the determination of Factor Xa. The following are known in particular among the tripeptide substrates which have been proposed for this purpose:

from EP-A-0 004 256 cited above,

Cbo-L-Pyr-Gly-L-Arg-pNA,
H-L-Pyr-Gly-L-Arg-pNA and their acid addition salts;
from EP-A-0 110 306, Z-D-Leu-Gly-L-Arg-pNA (presented as illustrating the prior art; see Table VIII on page 32 of said document EP-A-0 110 306), Z-D-Leu-Gly-L-Arg(2-OMe)pNA, Z-D-Leu-Gly-L-Arg(2-CONHMe)pNA, Z-D-Leu-Gly-L-Arg(2-COOBu)pNA, H-D-Lys(Z)-Gly-L-Arg(2-Z)pNA, Tos-Gly-L-Pro-L-Arg(2-CONHiPr)pNA and their addition salts; and
from U.S. Pat. Nos. 4,440,678 and 4,480,030 (which correspond to EP-A-0 034 122), the compounds of the formula

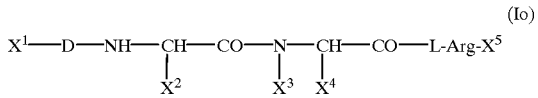

(Io)

in which

X$^1$ is C$_2$–C$_8$ alkanoyl, C$_2$–C$_8$ ω-aminoalkanoyl, phenylalkanoyl (in which the alkanoyl fragment is C$_2$–C$_4$ and the phenyl fragment can be substituted in the para position by NH$_2$), cyclohexylcarbonyl (which can be substituted in the 4 position by MeNH), benzoyl (which can be substituted in the ortho or para position), alkoxycarbonyl (in which the alkoxy fragment is C$_1$–C$_8$), benzyloxycarbonyl (in which the benzyloxy fragment can be substituted in the para position by MeO, Me or Cl), C$_1$–C$_4$ alkanesulfonyl, phenylsulfonyl (in which the phenyl fragment can be substituted in the para position by Me) or α- or β-naphthylsulfonyl, X$^2$ is C$_1$–C$_6$ alkyl with a linear or branched hydrocarbon chain, C$_1$–C$_2$ hydroxyalkyl, alkoxyalkyl (in which the alkoxy fragment is $C_1$–$C_4$ and the alkyl fragment is $C_1$–$C_2$), ω-carboxyalkyl or ω-alkoxycarbonylalkyl (in which the alkyl fragments are $C_1$–$C_3$ and the alkoxy fragment is $C_1$–$C_4$), ω-benzyloxycarbonylalkyl (in which the alkyl fragment is $C_1$–$C_3$), cyclohexyl, cyclohexylmethyl, 4-hydroxycyclohexylmethyl, phenyl, benzyl, 4-hydroxybenzyl or imidazol-4-ylmethyl, with the proviso that $X^1$ is other than the benzyloxycarbonyl group when $X^2$ is isopropyl or cyclohexyl, $X^3$ is $C_1$–$C_4$ alkyl, $X^4$ is H, Me or Et and $X^5$ is an aminated group containing an amino group substituted by an aromatic or heterocyclic radical, which can be cleaved by enzymic hydrolysis to give a colored or fluorescent compound H—$X^5$ detectable by photometry, spectrophotometry or fluorophotometry, the amount of H—$X^5$ released being proportional to the amount of enzyme causing the cleavage of the peptide substrate, and their acid addition salts.

The following tripeptides:

Cbo-D-CHG-Gly-L-Arg-pNA,
Cbo-D-CHT-MeGly-L-Arg-pNA,
Cbo-D-CHA-MeGly-L-Arg-pNA
Cbo-D-Nle-MeGly-L-Arg-pNA,
MeSO₂-D-CHA-Gly-L-Arg-pNA
Boc-D-AOA-Gly-L-Arg-pNA and their acid addition salts, may be mentioned in particular among the compounds of formula Io which have been proposed for the determination of Factor Xa.

The following are known in particular among the tetrapeptide compounds which have been described as substrates useful in the determination of Factor Xa:

the compound S-2222 (marketed by Kabi Diagnostica, Stockholm, Sweden), which has the formula Bz-L-Ile-Glu-Gly-L-Arg-pNA.HCl;

from CH-A-637 627 (corresponding to FR-A-2 372 798 cited above), the compounds

Bz-L-Ile-Glu(OMe)-Gly-L-Arg-pNA
Bz-L-Ile-Asp(Mor)-Gly-L-Arg-pNA and their acid addition salts; and from EP-A-0 010 306 cited above, Bz-L-Ile-L-Glu(OMe)-Gly-L-Arg-(2-CONHMe)pNA and its acid addition salts.

The prior art relating to the tri- or tetra-peptide substrates recommended for the determination of Factor Xa teaches that the specificity is a function of (i) the nature of the peptide chain, (ii) the structure of the blocking group at the N-terminal end, and (iii) the choice of cleavable developing group at the CO-terminal end of said chain.

SUBJECT OF THE INVENTION

According to the invention, a novel technical solution is recommended which differs from the prior art in the choice of a group which (i) blocks the N-terminal end of the peptide chain, and (ii) improves the solubility in water or the affinity for water of tri- or tetra-peptide compounds useful in the determination of Factor Xa.

Thus, according to a first feature of the invention, peptide compounds are recommended as novel industrial products, said compounds being selected from the group consisting of (i) the tri- and tetra-peptides of the formula, the tetra-peptide being identified as SEQ ID NO:1, $$Q\text{-}A_1\text{-}A_2\text{-}Gly\text{-}A_4\text{-}R \qquad (I)$$

in which

Q is a group which blocks the N-terminal end of the peptide chain and which is selected from the group consisting of (a) an oxymalonyl radical of the formula $R_1$—O—CO—$CH_2$—CO, in which $R_1$ is
    a $C_1$–$C_4$ alkyl group,
    a phenyl group,
    a phenyl group substituted by one or more Me, MeO, Cl, Br, F or $CF_3$ groups,
    a $C_3$–$C_6$ cycloalkyl group,
    a benzyl group,
    a benzyl group substituted by one or more Me, MeO, Cl, Br, F or $CF_3$ groups, or
    a cycloalkylmethyl group in which the cycloalkyl fragment is $C_3$–$C_6$; and (b) a polyethylene glycol residue of the formula $R_2$—$O(CH_2CH_2O)_n$—CO, in which $R_2$ is a $C_1$–$C_6$ alkyl, phenyl or benzyl group and n is an integer having a value of 1 to 170, $A_1$ is selected from the group consisting of Leu, Ile, Nle, Nva, CHA, CHG, CHT, Phe, Ala and Lys groups, where the basic side-group of the Lys residue is blocked with a suitable group which substantially removes the basic character of said side-group, $A_2$ is a single bond, Asp or Glu, the carboxylic acid side-group of Asp and Glu being capable of esterification or amidation, $A_4$ is selected from the group consisting of Arg and Lys groups, and R is a cleavable labeling means; and (ii) their addition salts.

According to a second feature of the invention, it is recommended to use the compounds of formula I and their acid addition salts as enzyme substrates for the determination of Factor Xa.

It has in fact been found, surprisingly, that the tri- and tetra-peptides according to the invention are more valuable than the tri- and tetra-peptide substrates known in the prior art in the field of the determination of Factor Xa, either because they are more active, or because they are more selective, or else because they are more water-soluble than said substrates of the prior art.

According to another feature of the invention, a method of preparing the compounds of formula I and their addition salts is recommended.

According to yet another feature of the invention, a method of determining Factor Xa by means of the compounds of formula I or their addition salts is provided.

Abbreviations

For convenience, the following abbreviations have been used in the present description:

the amino acid residues:

Ala=α-alanyl
β-Ala=β-alanyl
AOA=α-aminooctanoyl
Arg=arginyl Asp=α-aspartyl
CHA=3-cyclohexylalanyl CHG=α-cyclohexylglycyl
CHT=3-(4-hydroxycyclohexyl)alanyl
Ile=isoleucyl
Leu=leucyl
Lys=lysyl
MeGly=N-methylglycyl (or sarcosyl)
Nle=norleucyl
Nva=norvalyl
Phe=phenylalanyl
Pro=prolyl
Pyr=pyroglutaminyl (or pyrrolidin-2-one-5-carbonyl)
the other abbreviations:
Ac=acetyl
AcOH=acetic acid
Adoc=adamantyloxycarbonyl
Aoc=t-amyloxycarbonyl
Boc=t-butoxycarbonyl
Bop=(benzotriazol-1-yl)oxytris(dimethylamino) phosphonium hexafluorophosphate (alternative nomenclature: CASTRO's reagent) of the formula

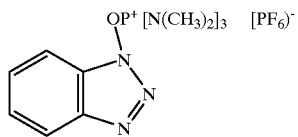

Bu=n-butyl
Bz=benzoyl
Bzl=benzyl
Cbo=carbobenzoxy
DCCI=dicyclohexylcarbodiimide
DIEA=diisopropylethylamine
DMF=dimethylformamide
Et=ethyl
EM=ethoxymalonyl (EtO—CO—$CH_2$—CO)
$Et_3N$=triethylamine
EtO=ethoxy
Fmoc=fluoren-9-ylmethoxycarbonyl
Foc=furfuryloxycarbonyl
HMPT=N,N,N',N',N'',N''-hexamethylphosphorotriamide
HOBT=1-hydroxybenzotriazole
HPLC=high performance liquid chromatography
H-TFA=trifluoroacetic acid (or HTFA)
Iboc=isobornyloxycarbonyl
iBu=isobutyl
iPr=isopropyl
Me=methyl
MeO=methoxy
MeOH=methanol
MM=methoxymalonyl (MeO—CO—$CH_2$—CO)
Mor=morpholin-1-yl
MW=molecular weight
OD=optical density
OSu=N-oxysuccinimide or (2,4-dioxopyrrolidin-1-yl)oxy
PEG=polyethylene glycol
Ph=phenyl
pH=cologarithm of the concentration of $H^+$ ions
Pi=piperidin-1-yl
pNA=p-nitroanilino or $(4-NO_2)C_6H_4NH$
Pr=n-propyl
Py=pyrrolidin-1-yl
RT=room temperature (15–20° C.)
tBu=t-butyl
THF=tetrahydrofuran
TLC=thin layer chromatography
Tos=p-toluenesulfonyl (or tosyl)
TR=retention time
Z=benzyloxycarbonyl
Z(p-Cl)=p-chlorobenzyloxycarbonyl
Z(p-OMe)=p-methoxybenzyloxycarbonyl

DETAILED DESCRIPTION OF THE INVENTION

As indicated above, the group Q is a group which blocks the N-terminal end of the peptide chain $A_1$-$A_2$-Gly-$A_4$, identified as SEQ ID NO: 1 (when residue $A_1$ is an amino acid in the L-configuration and $A_2$ is an Asp or Glu residue). It is an oxymalonyl radical of the formula $R_1$—O—CO—$CH_2$—CO or a PEG residue of the formula $R_2$—O$(CH_2CH_2O)_n$—CO. In said oxymalonyl radical, $R_1$ can be especially a $C_1$-$C_4$ alkyl group, preferably Me, Et, Pr, iPr, Bu or tBu, a phenyl group, a tolyl, xylyl, 2-, 3- or 4-methoxyphenyl, 2,4-, 2,6-, 3,4- or 3,5-dimethoxyphenyl, 4-chlorophenyl, 4-fluorophenyl, 3,4-, 3,5- or 2,6-dichlorophenyl or 3-trifluoromethylphenyl group, a cyclopropyl, cyclopentyl or cyclohexyl group, a benzyl group, a 2-, 3- or 4-methylbenzyl, 2-, 3- or 4-methoxybenzyl, 2,4-, 2,6-, 3,4- or 3,5-dimethylbenzyl, 2,4-, 2,6-, 3,4- or 3,5-dimethoxybenzyl, 2-, 3- or 4-chlorobenzyl, 2-, 3- or 4-fluorobenzyl, 2,4-, 2,6-, 3,4- or 3,5-dichlorobenzyl or 3-trifluoromethylbenzyl group, or a cyclopropylmethyl, cyclopentylmethyl or cyclohexylmethyl group.

When $R_1$ is a substituted phenyl or substituted benzyl group, the substituents will advantageously be located in the 2, 3 and/or 4 position. Even more advantageously, $R_1$ will be Me or Et so as to give the peptide compound a greater affinity for water; in other words, Q will then be MM or EM.

As regards the fragment $O(CH_2CH_2O)_n$ of the PEG residue, n will be an integer having a value of 1 to 170, as indicated above. In particular, the average MW of the fragment $O(CH_2CH_2O)_n$ will be between about 60 (n=1) and about 7100 (n=161). In said PEG residue, $R_2$ will advantageously be Me, Et, Pr, iPr, Bu, tBu or n-hexyl; even more advantageously, $R_2$ will be Me or Et.

As indicated above, $A_1$ is an amino acid residue selected from the group consisting of Leu, Ile, Nle, Nva, CHA, CHG, CHT, Phe, Ala and Lys, where the basic side-group of the Lys residue is blocked with a suitable acid group [such as Boc, Cbo, Z, Z(p-Cl), Z(p-OMe), Adoc, Aoc, Fmoc, Foc, Iboc]. In the case of the Lys residue, such an acid group makes it possible to remove the basic character of the basic side-group for practical purposes.

The residue $A_1$ can have the L or D configuration; however, for a better activity or sensitivity as regards the determination of Factor Xa, said residue $A_1$ preferably has the D configuration.

It is for this reason that $A_1$ will advantageously be selected from the group consisting of D-Leu, D-Ile, D-Nle, D-Nva, D-CHA, D-CHG, D-CHT, D-Phe, D-Ala and D-Lys groups, where the basic side-group of D-Lys is blocked with a suitable acid group.

The residues $A_1$ which are considered to be the most valuable according to the invention are D-Nle, D-Leu and D-CHA.

As indicated above, $A_2$ is a single bond or an Asp or Glu residue, it being possible, if appropriate, for the carboxyl side-group of each Asp and Glu residue to be esterified [i.e. for the OH group of the COOH group to be replaced with a group $OR_3$, in which $R_3$ is especially $C_1$–$C_4$ alkyl (for example Me, Et, iPr, Pr, Bu, tBu or iBu), $C_1$–$C_4$ hydroxyalkyl (preferably $CH_2CH_2$—OH), $C_3$–$C_6$ cycloalkyl (such as cyclopropyl, cyclopentyl or, preferably, cyclohexyl) or ω-aminoalkyl, in which the alkyl fragment is $C_2$–$C_4$ and in which the nitrogen atom of the amino fragment can be monoalkylated ($NHR_4$), dialkylated ($NR_4R_5$) or included in a ring ($NR_4R_5$=N-heterocyclic group)] or amidated [i.e. for the OH group of the COOH group to be replaced with a group $NH_2$, $NHR_4$ or $NR_4R_5$ (in which $R_4$ and $R_5$, which are identical or different, are each a $C_1$–$C_4$ alkyl group, it being possible for $R_4$ and $R_5$, taken together, to form, with the nitrogen atom to which they are bonded, a 5- to 7-membered N-heterocyclic group selected in particular from the group consisting of pyrrolidino, piperidino, morpholino, thiomorpholino, piperazino, 4-(2-hydroxyethyl)piperazino, 4-methylpiperazino, 4-(4-chlorophenyl)piperazino and hexamethyleneimino groups)].

Examples of Glu and Asp residues in which the COOH side-group is esterified or amidated are given in documents CH-A-637 627 and FR-A-2 372 798 cited above, which are incorporated here by way of reference.

Advantageously, when $A_2$ is an amino acid residue, said residue will have the L configuration; $A_2$ will therefore be either a single bond or a Glu or Asp residue selected especially from the group consisting of L-Glu, L-Asp, L-Glu(Mor), L-Glu(Py), L-Glu(Pi), L-Glu(OMe), L-Glu(OEt), L-Glu(OtBu), L-Asp(Mor), L-Asp-(Py), L-Asp(Pi), L-Asp(OMe), L-Asp(OEt) and L-Asp(OtBu) groups.

$A_4$ will also advantageously be L-Arg or L-Lys.

The labeling means R is well known in the art of biological and microbiological assays; reference is made in this connection to the prior art cited above and especially document U.S. Pat. No. 4,448,715. Said labeling means will preferably be selected from the group of aminated groups NH—R' which (i) induce a color change, (ii) induce a change in fluorescence, or (iii) contain at least one radioactive element (for example an anilino or benzylamino group labeled with a $^{14}C$ or $^3H$ radioisotope). Any amino group NH—R' which gives, during or after the enzymic reaction, a signal capable of being amplified for detection (for example by measurement of the optical density at a given wavelength, or by measurement of the radioactivity) is suitable for the purposes of the invention. The amount of product H—R obtained by cleavage in the enzymic hydrolysis is proportional to the amount of enzyme used. Said amount of H—R can be determined by photometry, spectrophotometry, fluorospectrophotometry or electrochemistry.

The group R which is preferred according to the invention is a chromogenic group, typically a nitrophenylamino group (in which the phenyl radical is capable of being substituted by a group COOH, F, Cl, Br, $CH_3$, $OCH_3$, CN, $CF_3$ and/or $SO_3H$), or a fluorogenic group, typically a naphthylamino group (in which the naphthyl radical is capable of being substituted by a group $OCH_3$, COOH, $SO_3H$ or $CH_3$), and 4-methylcoumaryl-7-amino, 4-trifluoromethylcoumaryl-7-amino and analogous groups.

The following may be mentioned in particular among the chromogenic and fluorogenic aminated groups which are suitable according to the invention: p-nitroanilino (abbreviated to pNA), 2-carboxy-4-nitroanilino and 3-carboxy-4-nitroanilino, 2-halogeno-4-nitroanilino and 3-halogeno-4-nitroanilino (in which the halogen is F, Cl or Br), 2-methoxy-5-methyl-4-nitroanilino, 2-hydroxysulfonyl-4-nitroanilino, 4-trifluoromethyl-2-nitroanilino, 4-trifluoromethyl-3-nitroanilino, 4-cyano-2-nitroanilino, naphthyl-2-amino, 4-hydroxysulfonylnaphthyl-1-amino, quinolylamino, nitroquinolylamino and the like.

The preferred group R according to the invention is a chromogenic group, namely on the one hand pNA and on the other hand analogous groups in which the phenyl ring of pNA is substituted in the 2 or 3 position, said groups having the formula

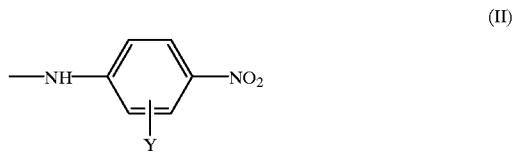

(II)

in which Y is Br, Cl, F, $CF_3$, COOH, COOW, $CONH_2$, CONHW, $CONW_2$, $CONH(CH_2)_m NMe_2$, OH or OW, in which W is a $C_3$–$C_6$ alkyl, $C_6$–$C_{10}$ aryl, $C_7$–$C_{11}$ aralkyl or $C_3$–$C_8$ alicyclic group and m is an integer having a value of 1 to 10.

Such groups of formula II in which the phenyl ring of the pNA group is substituted are described especially in document EP-A-0 110 306 cited above.

The addition salts according to the invention are essentially acid addition salts obtained by reacting a compound of formula I with a mineral or organic acid.

The best mode of carrying out the invention consists in using, as the substrate, a tri- or tetra-peptide compound of the formula $$Q-A_1-A_2-Gly-A_4-pNA \qquad (III)$$

in which

Q is MM, EM or $R_2$—$O(CH_2CH_2O)_n 13\ CO$, in which $R_2$ is Me, Et, Pr, iPr, Bu, iBu or n-hexyl and in which n is an integer of between 1 and about 161, $A_1$ is selected from the group consisting of D-Leu, D-Ile, D-Nle, D-Nva, D-CHA, D-CHG, D-CHT, D-Phe, D-Ala, D-Lys(Cbo) and D-Lys(Boc), the preferred groups $A_1$ being D-Nle, D-Leu and D-CHA, $A_2$ is selected from the group consisting of a single bond and L-Glu and L-Asp groups, in which the OH group of the carboxylic acid side-radical of said L-Glu and L-Asp can be replaced with OMe, OEt, OtBu, morpholino, piperidino or pyrrolidino, and $A_4$ is selected from the group consisting of L-Arg and L-Lys, and its acid addition salts.

Without implying a limitation, a number of peptide compounds (compounds "Ex.") according to the invention have been collated in Tables I and II below. For convenience, a reference peptide, which has been marketed as a substrate specific for Factor Xa, has also been included in Table I by way of comparison.

The peptide compounds according to the invention which have proved to be of particular value are especially the following:

(a) MM-D-Leu-Gly-L-Arg-pNA,
(b) EM-D-Leu-Gly-L-Arg-pNA,
(c) MeO(CH₂CH₂O)-CO-D-Leu-Gly-L-Arg-pNA,
(d) MeO(CH₂CH₂O)₂-CO-D-Leu-Gly-L-Arg-pNA,
(e) MeO(CH₂CH₂O)₃-CO-D-Leu-Gly-L-Arg-pNA,
(f) MeO(CH₂CH₂O)₇-CO-D-Leu-Gly-L-Arg-pNA,
(g) MM-D-Nle-Gly-L-Arg-pNA,
(h) MM-D-Nle-L-Glu(Py)-Gly-L-Arg-pNA,
(i) MM-D-CHA-Gly-L-Arg-pNA,
(j) MM-D-Ile-L-Glu(OMe)-Gly-L-Arg-pNA,
(k) EM-D-Nle-Gly-L-Arg-pNA and
(l) their acid addition salts.

TABLE I

Q—A₁—A₂-Gly-A₄—pNA.HA

| Product | Q | A₁ | A₂ | A₄ | HA |
|---|---|---|---|---|---|
| Ex. 1 | MM | D-Leu | — | L-Arg | AcOH |
| Ex. 2 | EM | D-Leu | — | L-Arg | AcOH |
| Ex. 3 | MM | D-CHA | — | L-Arg | AcOH |
| Ex. 4 | MM | D-Nle | — | L-Lys | AcOH |
| Ex. 5 | MM | D-CHT | — | L-Arg | AcOH |
| Ex. 6 | MM | D-Nva | — | L-Arg | AcOH |
| Ex. 7 | MM | D-CHG | — | L-Arg | HCl |
| Ex. 8 | MM | D-Phe | — | L-Arg | HCl |
| Ex. 9 | MM | D-Ala | — | L-Arg | HCl |
| Ex. 10 | MM | D-Ile | — | L-Arg | AcOH |
| Ex. 11 | MM | D-Lys(Cbo) | — | L-Arg | AcOH |
| Ex. 12 | MM | D-CHG | L-Asp(Py) | L-Lys | HCl |
| Ex. 13 | MM | D-CHT | — | L-Arg | H-TFA |
| Ex. 14 | MM | D-Nle | — | L-Arg | HCl |
| Ex. 15 | EM | D-CHA | — | L-Arg | HCl |
| Ex. 16 | EM | D-CHT | — | L-Arg | HCl |
| Ex. 17 | EM | D-Nva | — | L-Arg | AcOH |
| Ex. 18 | EM | D-CHG | — | L-Arg | AcOH |
| Ex. 19 | EM | D-Ala | — | L-Arg | AcOH |
| Ex. 20 | EM | D-Ile | — | L-Arg | HCl |
| Ex. 21 | EM | D-Nle | — | L-Arg | HCl |
| Ex. 22 | MM | D-Ile | — | L-Lys | AcOH |
| Ex. 23 | MM | D-CHG | — | L-Lys | AcOH |
| Ex. 24 | MM | D-Nva | — | L-Lys | HCl |
| Ex. 25 | MM | D-Lys(Boc) | — | L-Arg | AcOH |
| Ex. 26 | MM | D-Ala | — | L-Arg | HCl |
| Ex. 27 | MM | D-Nle | L-Glu(Py) | L-Arg | HCl |
| Ex. 28 | MM | D-Nle | L-Glu(OMe) | L-Arg | AcOH |
| Ex. 29 | MM | D-Nle | L-Asp(Py) | L-Arg | AcOH |
| Ex. 30 | MM | D-Nle | L-Glu | L-Arg | HCl |
| Ex. 31 | MM | D-Leu | L-Glu(OMe) | L-Arg | AcOH |
| Ex. 32 | MM | D-Ile | L-Glu | L-Arg | AcOH |
| Ex. 33 | MM | D-Ile | L-Glu(OMe) | L-Arg | AcOH |
| Ex. 34 | MM | D-Nva | L-Glu(Mor) | L-Arg | AcOH |
| Ex. 35 | MM | D-CHT | L-Asp(OMe) | L-Arg | AcOH |
| Ex. 36 | MM | D-Leu | L-Asp | L-Lys | AcOH |
| Ex. 37 | MM | D-Lys(Cbo) | L-Glu(Pi) | L-Arg | HCl |
| Ex. 38 | MM | D-Lys(Cbo) | L-Asp(Pi) | L-Arg | HCl |
| Ex. 39 | MM | D-CHA | L-Glu | L-Arg | AcOH |
| Ex. 40 | MM | D-CHG | L-Glu(Py) | L-Arg | AcOH |
| Ex. 41 | MM | D-Ala | L-Glu(OtBu) | L-Arg | AcOH |
| Ex. 42 | MM | D-Ala | L-Asp | L-Arg | AcOH |
| Ex. 43 | MM | D-Leu | L-Glu(Py) | L-Arg | HCl |
| Ex. 44 | MM | D-Leu | L-Asp(OMe) | L-Arg | HCl |
| Ex. 45 | MM | D-Ile | L-Asp(Py) | L-Arg | AcOH |
| Ex. 46 | MM | D-Phe | L-Glu | L-Arg | AcOH |
| Ex. 47 | MM | D-Phe | L-Glu(OMe) | L-Arg | AcOH |
| Ex. 48 | MM | D-Phe | L-Asp | L-Arg | HCl |
| Ex. 49 | MM | D-Phe | L-Asp(Pi) | L-Arg | HCl |
| Ex. 50 | MM | D-Nle | L-Glu(Mor) | L-Lys | AcOH |
| Ex. 51 | MM | D-Nle | L-Asp | L-Arg | AcOH |
| Ex. 52 | MM | D-Lys(Cbo) | L-Glu | L-Arg | AcOH |
| Ex. 53 | MM | D-Lys(Cbo) | L-Glu(OMe) | L-Arg | AcOH |
| Ex. 54 | MM | D-Lys(Cbo) | L-Glu(Py) | L-Arg | AcOH |
| Ex. 55 | MM | D-Lys(Cbo) | L-Asp | L-Arg | AcOH |
| Ex. 56 | MM | D-Lys(Cbo) | L-Asp(Py) | L-Arg | AcOH |
| Ex. 57 | MM | D-Nva | L-Glu(OMe) | L-Arg | AcOH |
| Ex. 58 | MM | D-Nva | L-Asp | L-Arg | AcOH |
| Ex. 59 | MM | D-CHG | L-Asp(Py) | L-Arg | AcOH |
| Ex. 60 | EM | D-CHG | L-Asp | L-Arg | AcOH |
| CP 1 | CH₃SO₂ | D-Leu | — | L-Arg | AcOH |

TABLE II

R₂—O(CH₂CH₂O)ₙ—CO—A₁—A₂-Gly-A₄—pNA.HA

| Product | R₂ | n | A₁ | A₂ | A₄ | HA |
|---|---|---|---|---|---|---|
| Ex. 61 | Me | 1 | D-Leu | — | L-Arg | AcOH |
| Ex. 62 | Me | 2 | D-Leu | — | L-Arg | AcOH |
| Ex. 63 | Me | 3 | D-Leu | — | L-Arg | AcOH |
| Ex. 64 | Me | 7 | D-Leu | — | L-Arg | AcOH |
| Ex. 65 | Me | 12 | D-Leu | — | L-Arg | AcOH |
| Ex. 66 | Me | 16 | D-Leu | — | L-Arg | AcOH |
| Ex. 67 | Me | 150 | D-Leu | — | L-Arg | AcOH |
| Ex. 68 | Me | 161 | D-Leu | — | L-Arg | AcOH |
| Ex. 69 | Me | 113 | D-Leu | — | L-Arg | AcOH |
| Ex. 70 | Me | 45 | D-Leu | — | L-Arg | AcOH |
| Ex. 71 | Me | 1 | D-Nle | — | L-Arg | AcOH |
| Ex. 72 | Me | 2 | D-Nle | — | L-Arg | AcOH |
| Ex. 73 | Me | 3 | D-Nle | — | L-Arg | AcOH |
| Ex. 74 | Me | 45 | D-Nle | — | L-Arg | AcOH |
| Ex. 75 | Me | 2 | D-CHA | — | L-Arg | AcOH |
| Ex. 76 | Me | 7 | D-CHA | — | L-Arg | AcOH |
| Ex. 77 | Me | 113 | D-CHA | — | L-Arg | AcOH |
| Ex. 78 | Me | 2 | D-CHT | — | L-Arg | AcOH |
| Ex. 79 | Me | 3 | D-CHT | — | L-Arg | AcOH |
| Ex. 80 | Me | 7 | D-Ala | — | L-Arg | AcOH |
| Ex. 81 | Me | 1 | D-Leu | L-Glu(Py) | L-Arg | HCl |
| Ex. 82 | Me | 7 | D-Leu | L-Glu(OMe) | L-Arg | HCl |
| Ex. 83 | Me | 16 | D-Leu | L-Glu(Pi) | L-Arg | HCl |
| Ex. 84 | Et | 2 | D-Nle | L-Asp(Py) | L-Arg | HCl |
| Ex. 85 | Et | 7 | D-Nle | L-Asp(OMe) | L-Arg | HCl |
| Ex. 86 | Et | 113 | D-Nle | L-Asp(Py) | L-Lys | HCl |
| Ex. 87 | Et | 2 | D-CHA | L-Glu(Py) | L-Lys | HCl |
| Ex. 88 | Et | 7 | D-CHA | L-Glu(OMe) | L-Lys | HCl |
| Ex. 89 | Et | 2 | D-CHA | L-Glu(Pi) | L-Lys | HCl |
| Ex. 90 | Et | 113 | D-CHA | L-Glu | L-Lys | HCl |
| Ex. 91 | Et | 2 | D-Lys(Cbo) | L-Glu | L-Arg | HCl |
| Ex. 92 | Et | 7 | D-Lys(Cbo) | L-Glu | L-Arg | HCl |
| Ex. 93 | Et | 2 | D-Nva | L-Glu | L-Arg | HCl |
| Ex. 94 | Et | 2 | D-Nva | L-Asp | L-Arg | HCl |
| Ex. 95 | Et | 7 | D-Phe | L-Glu | L-Arg | HCl |
| Ex. 96 | Et | 7 | D-Phe | L-Asp | L-Arg | HCl |
| Ex. 97 | Et | 7 | D-Ile | L-Glu | L-Arg | HCl |
| Ex. 98 | Et | 7 | D-CHG | L-Asp | L-Arg | HCl |
| Ex. 99 | Bu | 1 | D-Leu | — | L-Arg | HCl |
| Ex. 100 | Bu | 7 | D-Leu | — | L-Arg | HCl |
| Ex. 101 | Bu | 7 | D-Nle | — | L-Arg | AcOH |
| Ex. 102 | Bu | 12 | D-Nle | — | L-Arg | AcOH |
| Ex. 103 | n-hexyl | 1 | D-Leu | — | L-Arg | AcOH |
| Ex. 104 | n-hexyl | 7 | D-Leu | — | L-Arg | AcOH |
| Ex. 105 | n-hexyl | 1 | D-CHA | — | L-Arg | AcOH |
| Ex. 106 | n-hexyl | 7 | D-CHA | — | L-Arg | AcOH |

The tri- and tetra-peptide compounds according to the invention can be prepared in accordance with a method known per se by the application of conventional reaction mechanisms. The method of preparation which is recommended here comprises reacting a peptide of the formula $$H\text{-}A_1\text{-}A_2\text{-}Gly\text{-}A_4\text{-}R \qquad (IV)$$

in which $A_1$, $A_2$, $A_4$ and R are defined as indicated above, with a substance selected from the group consisting of
a) the oxymalonyl derivatives of the formula $$R_1\text{—O—CO—}CH_2\text{—CO—T} \qquad (V)$$

in which $R_1$ is defined as indicated above and T is OH, F, Cl or Br, and b) the PEG derivatives of the formula $$R_2\text{-O(CH}_2\text{CH}_2\text{O)}_n\text{-CO-Hal} \tag{VI}$$

in which $R_2$ and n are as defined above and Hal is F, Cl or Br.

The reactions IV+V=I and IV+VI=I are each carried out in an inert solvent such as DMF or THF, in the presence of an excess of a base acting as a cosolvent and as a proton acceptor, such as $Et_3N$, DIEA or any other suitable tertiary amine.

In practice, to carry out the reaction IV+V=I, two different techniques are recommended according to the nature of the group T. When T is F, Cl or Br, a molar ratio IV/V which is less than or equal to 1/2 will be used. When T is OH, the reaction will also be carried out in the presence of a coupling agent such as Bop or HOBT (DCCI being added, if appropriate, to the coupling agent HOBT where the latter is used), at a temperature of about 0° C. for at least 1 hour and then at RT for at least 24 hours, with a molar ratio IV/V in the range from 1/1 to 1/1.5.

Furthermore, when T is F, Cl or Br in said reaction IV+V=I, a molar ratio $IV/Et_3N$ of between 1.7/1 and 3.6/1 and preferably of 2/1 to 3.1/1 will be used.

In practice, the reaction IV+VI=I will be carried out with a molar ratio IV/VI which is less than or equal to 1 and preferably less than or equal to 0.8.

To carry out the reaction IV+VI=I, it is preferred to use a derivative of formula VI in which Hal is Cl. Such a chlorinated derivative, used as a starting material for said reaction IV+VI=I, can be synthesized according to the following reaction scheme:

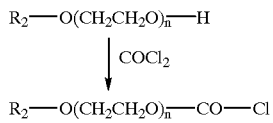

On the one hand the compounds of formula V are prepared from malonic acid and on the other hand the compounds of formula IV are obtained by a conventional method of peptide synthesis such as described especially in document EP-A-0 280 610 cited above.

The compounds according to the invention are useful in the determination of Factor Xa. An assay kit for the determination of Factor Xa, which contains at least one peptide compound selected from the group consisting of the compounds of formula I and their addition salts and, if appropriate, a standard sample of Factor Xa and of buffered dilution media, is therefore also recommended.

A method of determining Factor Xa is also recommended, wherein a given amount of a compound of formula I or of one of its addition salts is brought into contact, in an aqueous biological medium, with a test sample (diluted if appropriate) which may contain Factor Xa.

Further advantages and characteristics of the invention will be understood more clearly from the following description of Preparatory Examples and results of comparative tests. These data as a whole do not in any way imply a limitation but are given by way of illustration.

Preparation I

Preparation of MM-D-Leu-Gly-L-Arg-pNA.AcOH (Example 1)

a) Z-L-Arg-pNA.HCl 344 g (1 mol) of Z-L-Arg-OH.HCl are dissolved in anhydrous HMPT (freshly distilled and dried over a molecular sieve) at RT and 139 ml (1 mol) of $Et_3N$ are then added at RT, with stirring. 328 g (2 mol) of p-nitrophenyl isocyanate are added to the resulting solution. The resulting reaction medium is stirred for 24 h at RT and then evaporated under vacuum and the residue is taken up with the minimum amount of AcOH and then diluted with AcOEt. The resulting solution is subsequently extracted successively three times with small amounts of 0.5 M $NaHCO_3$, three times with a solution of $KHSO_4$ at 50 g/l and then several times with $H_2O$ semisaturated with NaCl. The organic phase is then dried over anhydrous sodium sulfate. After filtration (removal of $Na_2SO_4$), the solvent is evaporated off and the evaporation residue is recrystallized from an AcOEt/MeOMe mixture (3/7 v/v) to give 350 g of the expected product in the form of a white powder. M.p.= 128–130° C.

Analysis (TLC on silica gel):

Rf=0.5 in $AcOEt/pyridine/AcOH/H_2O$ (20/4.5/3/1 v/v);
Rf=0.69 in $CHCl_3/MeOH/AcOH$ (5/3/1 v/v).

b) H-L-Arg-pNA.2HBr 100 g (0.215 mol) of Z-L-Arg-pNA.HCl are charged into a glass/Teflon apparatus. 800 ml of glacial AcOH, 200 ml of anisole and 1000 ml of a solution of HBr in glacial AcOH are added successively under an inert atmosphere (stream of nitrogen). The reaction is left to proceed for 1 h at RT under a nitrogen atmosphere. After this time has elapsed, the reaction mixture, which has become homogeneous during the deprotection, is precipitated in 20 l of ether (MeOMe or EtOEt). After decantation, the supernatant is discarded and the precipitate is washed several times with ether. The precipitate is collected by filtration and dried under vacuum over KOH for 24 h to give 94.2 g (yield: 96%) of the expected product.

Analysis (TLC on silica gel):

Rf=0.04 in $AcOEt/pyridine/AcOH/H_2O$ (20/4.5/3/1.5 v/v);
Rf=0.38 in $BuOH/AcOH/H_2O$ (3/1/1 v/v).

c) Boc-Gly-L-Arg-DNA.HBr 1 g (2.19 mmol) of H-L-Arg-pNA.2HBr is dissolved in 10 ml of DMF, and 0.854 ml (6.57 mmol) of DIEA is then added. In another vessel, a solution of 384 mg (2.19 mmol) of Boc-Gly-OH in 5 ml of DMF is neutralized with 0.285 ml of DIEA. The two solutions obtained in this way are mixed and 970 mg of Bop are added to the resulting medium, the latter being kept at RT; also, the pH is kept at a value of between 7 and 8 by the addition of small portions of DIEA throughout the reaction. After one hour, the reaction has completely finished and the reaction medium is evaporated to dryness under vacuum; the evaporation residue is taken up with an AcOEt/MeOH mixture and extracted with a 0.5 M aqueous solution of $NaHCO_3$. The organic phase is dried over sodium sulfate, concentrated under vacuum and then precipitated in ether (MeOMe or EtOEt) to give 874 mg (yield: 75%) of the expected product.

Analysis (TLC on silica gel):
Rf=0.53 in CHCl$_3$/MeOH/AcOH (10/3/1 v/v).

d) H-Gly-L-Arg-pNA.2H-TFA 874 mg (1.64 mmol) of Boc-Gly-L-Arg-pNA.HBr are charged into a reactor and 6.6 ml of CH$_2$Cl$_2$ and 6.6 ml of H-TFA are then added successively. After a reaction time of 0.25 h at RT, the reaction mixture is precipitated directly in ether. A flaky white precipitate is formed which is filtered off and dried to give 910 mg (yield: 96%) of the expected product.

Analysis (TLC on silica gel):
Rf=0.09 in CHCl/MeOH/AcOH (5/3/1 v/v).

e) Boc-D-Leu-Gly-L-Arg-DNA.H-TFA

Following the procedures of Preparation Ic, a reaction mixture comprising (i) 910 mg (1.57 mmol) of H-Gly-L-Arg-pNA.2H-TFA, (ii) 363 mg (1.57 mmol) of Boc-D-Leu-OH, (iii) 1.2 ml of DIEA and (iv) 695 mg (1.57 mmol) of Bop is reacted in DMF and the reaction mixture is kept at RT for 2 h, with stirring. After evaporation to dryness under vacuum, the evaporation residue is chromatographed on silica gel using a CHCl$_3$/MeOH/AcOH gradient (20/3/1 to 10/3/1 v/v) as the eluent. The homogeneous fractions collected are pooled and the eluent is evaporated off. Lyophilization gives 785 mg (yield: 80%) of the expected product in pure form.

Analysis (TLC on silica gel):
Rf=0.33 in CHCl$_3$/MeOH/AcOH (10/3/1 v/v).

f) H-D-Leu-Gly-L-Ara-pNA.2H-TFA 785 mg (1.25 mmol) of Boc-D-Leu-Gly-L-Arg-pNA.H-TFA, obtained according to Preparation Ie, are reacted with 5 ml of CH$_2$Cl$_2$ and 5 ml of H-TFA at RT. After 0.25 h, the reaction mixture is precipitated directly in ether to give a white precipitate, which is filtered off, washed with ether and dried. 779 mg (yield: 90%) of the expected product are collected.

Analysis (TLC on silica gel):
Rf=0.2 in CHCl$_3$/MeOH/AcOH (5/3/1 v/v).

g) MM-D-Leu-Gly-L-Arg-pNA.AcOH 7.79 mg (1.12 mmol) of H-D-Leu-Gly-L-Arg-pNA.2H-TFA are charged into a reaction vessel and 15 ml of DMF and 0.517 ml (3.705 mmnol) of Et$_3$N are then added. The resulting mixture is cooled to −30° C., with stirring, and 0.265 ml of methoxymalonyl chloride (MeO—CO—CH$_2$—CO—Cl) is then added dropwise (still with stirring and at −30° C). The resulting mixture is kept at −30° C. for 0.5 h and then allowed to warm up to RT. After a reaction time of 2 h, the reaction mixture is filtered to remove the triethylammonium salt which has formed, and the filtrate is evaporated under vacuum. The evaporation residue is precipitated with ether (EtoEt), filtered off and then chromatographed on an ion exchange resin (AMBERLITE® IRA 401 S) acetylated beforehand, using an MeOH/H$_2$O mixture (3/2 v/v) as the eluent. The homogeneous fractions are pooled and evaporated. Lyophilization of the resulting evaporation residue gives 566 mg (yield: 81%) of the expected product.

Analysis:
TLC on silica gel:
Rf=0.71 in CHCl$_3$/MeOH/AcOH (10/3/1 v/v);
HPLC [on a column of HYPERSIL® C 18 (particle size: 3 μm) supplied by MERCK]:
TR=10 minutes [with an isocratic solution containing water (72.4%), acetonitrile (27.5%) and ACOH (0.2% w/w)].

Preparation II
Preparation of MM-D-Leu-L-Arg-pNA.AcOH (Example 1)

The procedure indicated in Preparation I is followed except that step Ig is replaced with the following step:

1391 mg (2 mmol) of H-D-Leu-Gly-L-Arg-pNA.2H-TFA are charged into a reaction vessel and 30 ml of DMF and 0.7 ml (5 mmol) of Et$_3$N are then added. 973.5 mg of Bop are added at room temperature and a solution of 259 mg of methoxymalonic acid (MeO—CO—CH$_2$—CO—OH) in 10 ml of DMF and 0.7 ml of Et$_3$N is then added to the resulting mixture. As the reaction proceeds, the pH is kept between 7 and 8 during the coupling by the successive addition of small amounts of Et$_3$N; after a reaction time of 3 h, with stirring, the coupling is complete. The reaction medium is extracted with a solvent system of AcOEt/KHSO$_4$ (at 5% w/v) and then AcOEt/0.5 M NaHCO$_3$. The AcOEt phase is then washed with water semisaturated with NaCl. The AcOEt phase is evaporated under vacuum and the evaporation residue is then chromatographed on a column of silica (particle size: 40–60 micrometers) using CHCl$_3$/MeOH/AcOH (8/3/1 v/v) as the eluent system. The homogeneous fractions are pooled and evaporated. Lyophilization of the resulting evaporation residue gives 812 mg (yield: 65%) of the expected product.

Analysis:
TLC on silica gel:
Rf=0.71 in CHCl$_3$/MeOH/AcOH (10/3/1 v/v);
HPLC [as indicated above in step Ig]:
TR=10 minutes.

Preparation III
Preparation of Me-OCH$_2$CH$_2$O-CO-D-Leu-Gly-L-Arg-pNA.AcOH (Example 61)

a) Et—OCH$_2$CH$_2$O—CO—Cl

Phosgene is condensed in a reactor at a temperature of −30° C. and 10 ml of ethylene glycol monomethyl ether, dissolved beforehand in THF, are then added dropwise (still at −30° C.), by means of a dropping funnel, so that the phosgene is always in large excess relative to the alcohol. The reaction medium is stirred at −30° C. for 2 h and then allowed to warm up to RT. The excess phosgene is removed with a stream of nitrogen, the operation lasting several hours so that every trace of said phosgene is removed. The reaction mixture is then evaporated under vacuum and the liquid obtained is used as such in the subsequent coupling step to give 1320 mg (yield: 95%) of the expected product.

Analysis (IR spectrum):
disappearance of the alcohol band at 3300 cm$^{-1}$;
appearance of the chloroformate bands at 1776, 1152 and 690 cm$^{-1}$.

Comment: The method of step IIIa can be used directly to give the other chloroformates of the formula R$_2$—O(CH$_2$CH$_2$O)$_n$—CO—Cl.

b) MeOCH$_2$CH$_2$O-CO-D-Leu-Gly-L-Arg-pNA.AcOH 1391 mg (2 mmol) of H-D-Leu-Gly-L-Arg-pNA.2H-TFA (obtained as indicated in Preparation If) are charged into a reaction vessel and 30 ml of DMF and 0.624 ml of Et$_3$N are then added. The resulting mixture is cooled to 0° C. by means of an ice bath. 0.304 g (2.2 mmol) of the chloroformate MeOCH$_2$CH$_2$O—CO—Cl is added to said mixture cooled in this way. The reaction medium is stirred for 1 h and allowed to warm up to RT and the reaction is then continued for 1 h at RT. The reaction mixture is then filtered and evaporated under vacuum and the evaporation residue is chromatographed on an ion exchange resin (AMBERLITE® IRA 400 S) acetylated beforehand, using an MeOH/H$_2$O mixture (3/2 v/v) as the eluent. The homogeneous fractions are pooled and evaporated. Lyophilization of the resulting evaporation residue gives 814 mg (yield: 65%) of the expected product.
Analysis:
TLC on silica gel:
Rf=0.65 in $CHCl_3$/MeOH/AcOH (10/3/1 v/v).
Preparation IV
Preparation of Me-O($CH_2CH_2O$)$_7$-CO-D-Leu-Gly-L-Arg-pNA.AcOH (Example 64)

The procedure indicated in Preparation IIIb is followed except that the Me—$OCH_2CH_2O$—CO—Cl is replaced with MeO($CH_2CH_2O$)$_7$—COCl to give 1.038 g (yield: 61%) of the expected product.

Analysis (TLC on silica gel):
Rf=0.61 in $CHCl_3$/MeOH/AcOH (10/3/1 v/v);
Rf=0.14 in $CHCl_3$/MeOH/AcOH (20/3/1 v/v).
Preparation V
Preparation of Me-O($CH_2CH_2O$)$_2$-CO-D-Leu-Gly-L-Arg-pNA.AcOH (Example 62)

The procedure indicated in Preparation IIIb is followed except that the Me—$OCH_2CH_2O$—CO—Cl is replaced with MeO($CH_2CH_2O$)$_2$—COCl to give 851 mg (yield: 68%) of the expected product.

Analysis (TLC on silica gel):
Rf=0.45 in $CHCl_3$/MeOH/AcOH (15/3/1 v/v).
Comparative Tests The activity of the peptides according to the invention towards Factor Xa was determined by one of the conventional methods, such as the one described in EP-A-0 280 160 (see page 14), the hydrolysis rate being assessed by the variation in optical density with time ($\Delta$OD/min). The results obtained at equimolar doses have been collated in Table III below, where the activity of the reference product CP 1 is specified as being equal to 100% for the sake of convenience.

The comparative results in Table III show that the peptides according to the invention are at least as active as the reference product CP 1.

TABLE III

| ACTIVITY TOWARDS FACTOR Xa | |
|---|---|
| Product | Activity |
| Ex. 1 | 115% |
| Ex. 2 | 132% |
| Ex. 14 | 140% |
| Ex. 33 | 105% |
| Ex. 61 | 145% |
| Ex. 62 | 105% |
| Ex. 63 | 110% |
| Ex. 64 | 103% |
| Ex. 73 | 121% |
| Ex. 101 | 124% |
| CP 1 | 100% |

What is claimed is:

1. A peptide compound selected from the group consisting of
   (a) MM-D-Leu-Gly-L-Arg-pNA,
   (b) EM-D-Leu-Gly-L-Arg-pNA,
   (c) MeO(CH$_2$CH$_2$O)-CO-D-Leu-Gly-L-Arg-pNA,
   (d) MeO(CH$_2$CH$_2$O)$_3$-D-Nle-Gly-L-Arg-pNA,
   (e) BuO(CH$_2$CH$_2$O)$_7$-D-Nle-Gly-L-Arg-pNA,
   (f) MM-D-CRA-Gly-L-Arg-pNA,
   (g) MM-D-Nle-Gly-L-Arg-pNA, and
   (h) their acid addition salts.

2. A method of determining Factor Xa, wherein a given amount of a peptide compound according to claim 1 or of one of its addition salts is brought into contact, in an aqueous biological medium, with a test sample which may contain Factor Xa.

3. An assay kit for the determination of Factor Xa, which contains at least one peptide compound selected from the group consisting of the compounds of formula I and their addition salts according to claim 1 and, if appropriate, a standard sample of Factor Xa and of buffered dilution media.

* * * * *